United States Patent
Akhavan-Tafti

(10) Patent No.: US 7,129,045 B2
(45) Date of Patent: *Oct. 31, 2006

(54) METHODS OF DETECTING POLYNUCLEOTIDE KINASE AND ITS USE AS A LABEL

(75) Inventor: Hashem Akhavan-Tafti, Howell, MI (US)

(73) Assignee: Lumigen, Inc., Southfield, MI (US)

( * ) Notice: Subject to any disclaimer, the term of this patent is extended or adjusted under 35 U.S.C. 154(b) by 803 days.

This patent is subject to a terminal disclaimer.

(21) Appl. No.: 09/979,215

(22) PCT Filed: Mar. 23, 2001

(86) PCT No.: PCT/US01/08621

§ 371 (c)(1),
(2), (4) Date: Nov. 21, 2001

(87) PCT Pub. No.: WO01/71037

PCT Pub. Date: Sep. 27, 2001

(65) Prior Publication Data

US 2004/0253585 A1      Dec. 16, 2004

Related U.S. Application Data

(60) Provisional application No. 60/191,621, filed on Mar. 23, 2000.

(51) Int. Cl.
*C12Q 1/68* (2006.01)
*C12P 19/34* (2006.01)
*C07H 21/04* (2006.01)

(52) U.S. Cl. .................. 435/6; 435/91.2; 435/91.5; 435/91.51; 536/25.32; 536/25.3

(58) Field of Classification Search .............. 435/6, 435/91.2, 91.5, 91.52; 536/25.32, 25.3, 25, 536/32

See application file for complete search history.

(56) References Cited

U.S. PATENT DOCUMENTS

| | | | | |
|---|---|---|---|---|
| 5,512,439 | A | * | 4/1996 | Hornes et al. .................. 435/6 |
| 5,599,921 | A | * | 2/1997 | Sorge et al. ............... 536/24.33 |
| 5,804,375 | A | | 9/1998 | Gelfand |
| 5,998,175 | A | | 12/1999 | Akhavan-Tafti |
| 6,001,614 | A | | 12/1999 | Akhavan-Tafti |
| 6,013,456 | A | | 1/2000 | Akhavan-Tafti |
| 6,020,138 | A | | 2/2000 | Akhavan-Tafti |

OTHER PUBLICATIONS

C.E. Pritchard, E.M. Southern, Nucl. Acids Res., 25 3403-3407 (1997).

* cited by examiner

*Primary Examiner*—Kenneth R. Horlick
*Assistant Examiner*—Joyce Tung
(74) *Attorney, Agent, or Firm*—Richard S. Handley

(57) ABSTRACT

Methods of detecting or measuring the activity of polynucleotide kinase are disclosed as well as methods of detecting an analyte in an assay using polynucleotide kinase as a label on a member of a specific binding pair. The methods rely on the phosphorylation of an oligonucleotide followed by ligation of the oligonucleotide 5'-phosphate onto another template-bound oligonucleotide. The presence of the ligated product signals the presence of polynucleotide kinase. In preferred embodiments, phosphorylation of an oligonucleotide enables the consecutive ligation of a set of oligonucleotides. The oligonucleotides so ligated can be detectably labeled with, for example, other enzymes to provide highly sensitive detection methods.

25 Claims, 9 Drawing Sheets

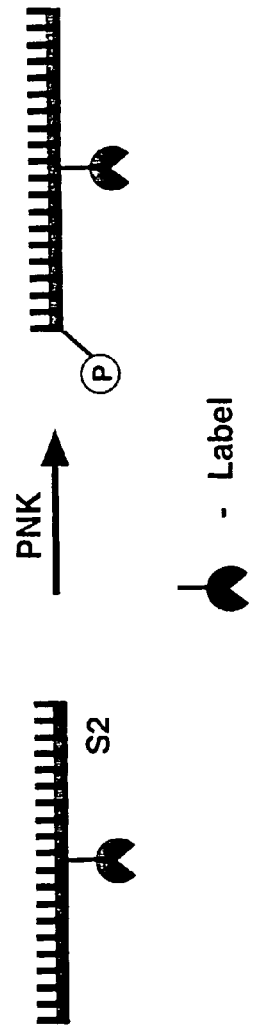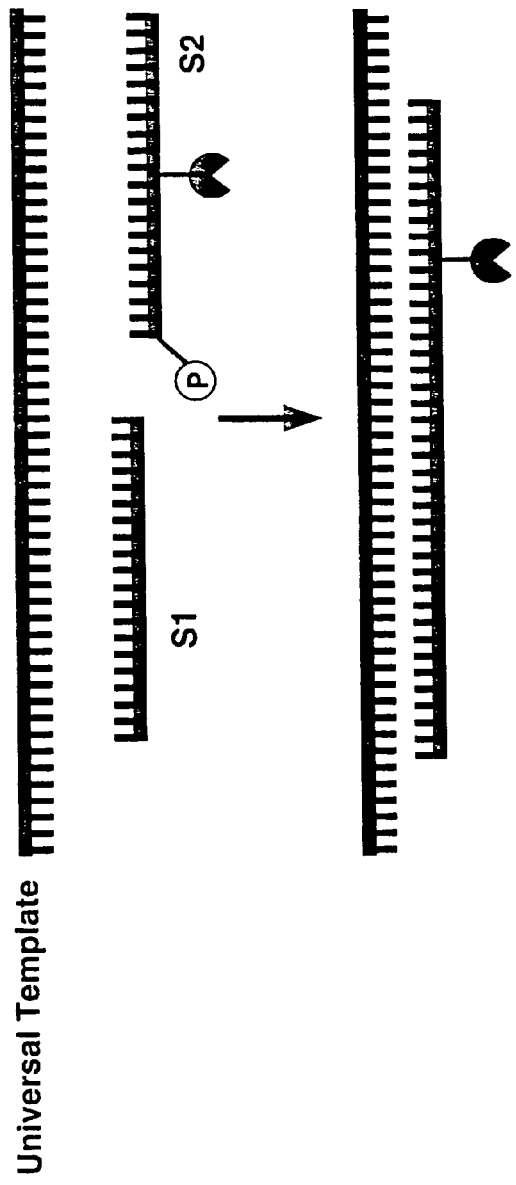
FIG. 2A
FIG. 2B

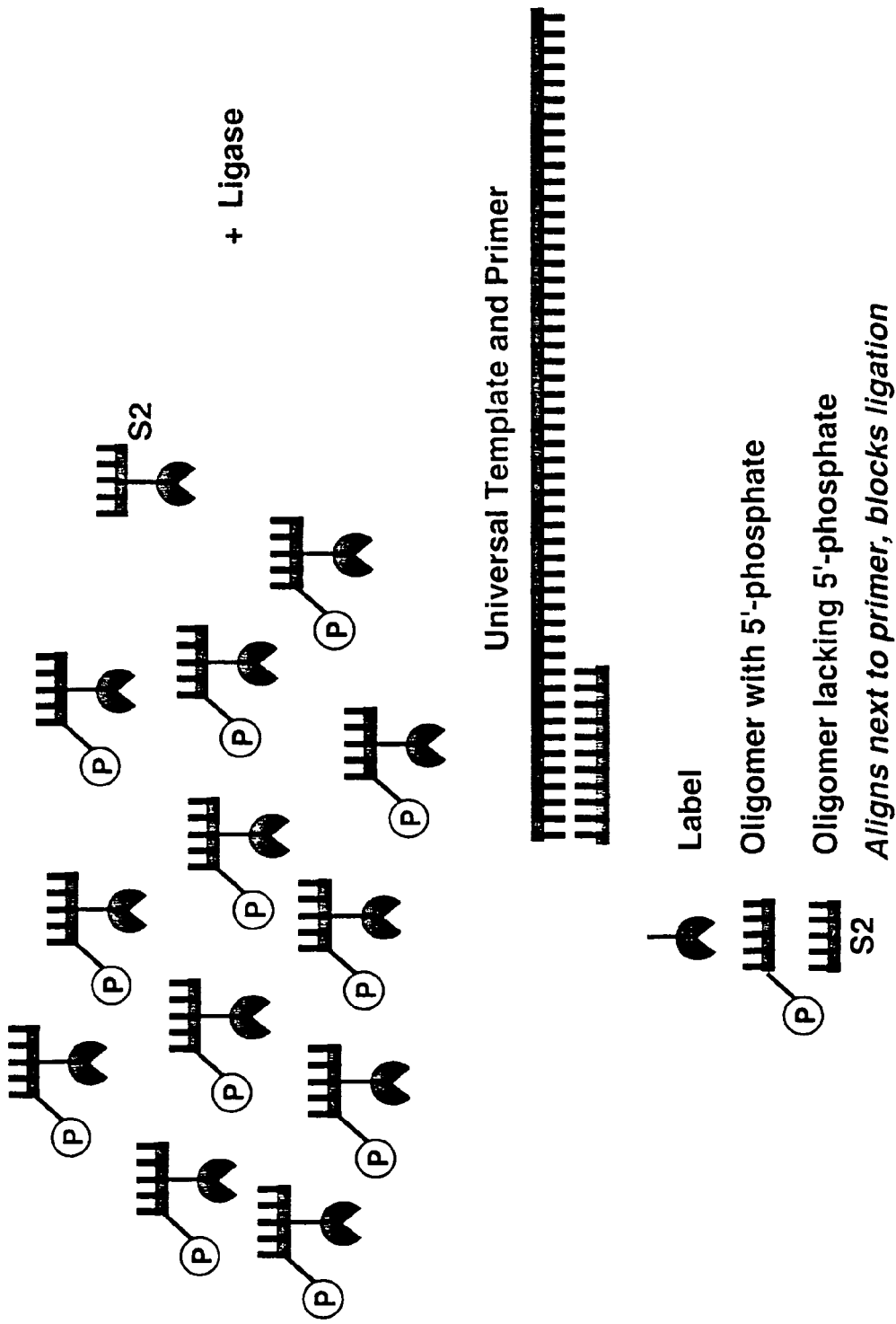

Multiply labeled complement contains a handle to bind additional multiply labeled signal probes FIG. 9
0          8.9 x 10⁻⁵
    
6.2 x 10⁻⁴    4.4 x 10⁻³
    
3.1 x 10⁻²    2.1 x 10⁻¹
Units of PNK used ized as methods of detection using the enzyme polynucleotide kinase (PNK) as a reporter or label on a specific binding partner. The present invention also relates to methods of measuring the activity of PNK. In the methods, PNK serves as a catalyst for the phosphorylation of one or more detector oligonucleotides which are subsequently ligated to produce a detectable species. The methods of the invention are useful in a variety of applications, including diagnostic assays such as immunoassays and nucleic acid hybridization assays, mutation analysis and gene expression monitoring.

BACKGROUND OF THE INVENTION

PNK catalyzes the transfer of the γ-phosphate of ATP to the 5'-hydroxyl group of DNA, RNA, shorter oligonucleotides and nucleotide-3'-phosphates. Because of this activity it is widely used in molecular biological methods. The activity of PNK is measured for the purpose of assessing the quality of enzyme preparations. Typical methods utilize $\gamma$-$^{32}$P ATP as the phosphate source and determine the amount of the radiolabel incorporated into the product by such means of thin layer chromatography followed by scintillation counting. Quantitative assays involving phosphorylation of polynucleotides or oligonucleotides followed by ligation and detection of ligated products have not been reported to the best of Applicant's knowledge.

Numerous enzyme-linked assay methods have been devised for the sensitive detection of a wide variety of analytes. Enzyme-linked methods are now widely used in the fields of immunoassay and DNA probe assays. The chief impetus behind the development of these methods is the improvement of sensitivity due to signal amplification afforded by the catalytic turnover of substrate to produce a detectable product. The most commonly used enzymes are alkaline phosphatase, β-galactosidase and horseradish peroxidase (L. J. Kricka, *Ligand-Binder Assays*, Marcel Dekker, Inc., New York, 1985, Chapter 6, pp. 165–198; C. A. Dangler, *Nucleic Acid Analysis*, Wiley-Liss., New York, 1996, Chapter 3, pp. 47–66). PNK does not appear to have been used as a label in these types of assays.

The enzymatic ligation of pairs of oligonucleotides bound to a target nucleic acid is a widely used method, finding application in for example the ligase chain reaction (LCR), methods for circularizing nucleic acids and in hybridization assays where a capture oligonucleotide is linked to a signal oligonucleotide when hybridized to a target. It is generally thought that the oligonucleotides must each be of a minimum length to be ligated efficiently. Recent work has shown this minimum length to be about 6–8 bases (C. E. Pritchard and E. M. Southern, Nucl. Acids Res., 25, 3403–3407 (1997)). Typically, much longer nucleic acids are employed.

Applicant's U.S. Pat. Nos. 5,998,175, 6,001,614, 6,013,346 and 6,020,138, which are fully incorporated herein by reference, disclose methods for sequentially ligating a plurality of oligonucleotides onto a hybridized "primer" or anchor oligonucleotide in one step under conditions where only the anchoring oligonucleotide is stably hybridized. An advantage of this sequential multiple ligation technique is that many detectably labeled units are able to be added onto the product nucleic acid under highly controlled conditions. Ligation only occurs when the anchoring oligonucleotide is hybridized and all oligonucleotides are of the correct sequence to align in a contiguous manner on the template.

SUMMARY OF THE INVENTION

It is an object of the present invention to provide methods of detection of analytes.

It is a further object of the present invention to provide methods of detection using the enzyme PNK as a reporter or label on a specific binding partner.

It is another object of the present invention to provide methods of measuring the activity of PNK.

It is another object of the present invention to provide methods measuring the activity of PNK by phosphorylation of oligonucleotides and ligating two or more oligonucleotides together to produce a ligated nucleic acid product.

It is another object of the present invention to produce a detectably labeled nucleic acid product by ligation of at least two oligonucleotides wherein at least one oligonucleotide has been phosphorylated at a 5'-OH group by PNK. It is another object of the present invention to produce the detectably labeled nucleic acid product with at least one enzyme label.

GENERAL DESCRIPTION

The present invention provides a new method of measuring the activity of PNK based on the phosphorylation of the 5'-OH of an oligonucleotide, polynucleotide or nucleic acid, having a sequence S2, where the presence of the 5'-phosphate group permits ligation of the oligonucleotide, polynucleotide or nucleic acid onto another oligonucleotide, polynucleotide or nucleic acid, having a sequence S1, which is hybridized with a complementary oligonucleotide, polynucleotide or nucleic acid containing adjacent sequences C1 and C2 which are the complements or S1 and S2. In one embodiment, a set of n contiguous oligonucleotides having sequences S2–Sn are provided wherein the oligonucleotide having sequence S2 has a 5'-OH group, the oligonucleotides having sequence S3–Sn have a 5'-phosphate and the complementary oligonucleotide contains contiguous complementary sequences C1–Cn. Phosphorylation of the oligonucleotide having sequence S2 permits all of the oligonucleotides to be ligated together. In the absence of PNK, no phosphorylation occurs, therefore none of the oligonucleotides are ligated.

Preferably, some of the oligonucleotides are detectably labeled. The creation of ligation product presents the means of assessing the activity, since no ligated product can form until the oligonucleotide having sequence S2 becomes phosphorylated. The ligated product can be detected by virtue of its length, by inclusion of a radioisotope such as a $^{32}$P or $^{33}$P in the internucleotide bond. The latter would result from the use of $\gamma$-$^{32}$P or $\gamma$-$^{33}$P ATP in the phosphorylation reaction catalyzed by PNK. One or more of the oligonucleotides incorporated into the ligation product can bear a detectable label. In this case, detection of the presence of label signifies the success of ligation and therefore the occurrence of phosphorylation.

The present methods are useful in their own right for detecting or measuring the activity of PNK. The methods could find use for example as a quality control measure for assaying the activity of commercial preparations of the enzyme. The methods are of further use when PNK is employed as a label to report the presence of a substance to be analyzed in an assay. In these embodiments PNK is covalently linked to a member of a specific binding pair such as an antibody, antigen or nucleic acid probe. The linkage may either be by direct conjugation or by means of secondary specific binding pairs. An example would be to use a primary specific binding partner for an analyte of interest which is labeled with biotin or a small hapten and a PNK-streptavidin or PNK-antibody conjugate.

When using the methods of the present invention wherein the PNK is provided as a label in an assay of an analyte in a sample, the amount of PNK detected by virtue of the subsequent phosphorylation-ligation reaction is correlated to the amount of analyte in the sample in the customary manner. As in all enzyme-coupled detection schemes an amplification is expected since PNK functions catalytically to phosphorylate its substrate. This will be the case in the present methods provided that the phosphate donor, typically ATP, and an oligonucleotide with a 5'-OH are provided in large excess. The methods are capable of providing very high sensitivity because a second stage of signal amplification is imparted when multiple labeled oligonucleotides are ligated in the ligation step. Further, if the detectable label is an enzyme, a third stage of amplification will result as this label enzyme catalyzes formation of a detectable product. In this aspect, the method can be viewed as an enzyme cascade reaction scheme.

BRIEF DESCRIPTION OF THE DRAWINGS

FIG. 2 depicts the phosphorylation and ligation steps involved in the present methods. FIG. 2A represents the phosphorylation of a labeled oligonucleotide at the 5'-terminus. FIG. 2B depicts the ligation of the labeled oligonucleotide 5'-phosphate onto a template-bound first oligonucleotide.

FIG. 3 depicts an embodiment wherein a set of oligonucleotides is used for ligation onto a template-bound first oligonucleotide. All oligonucleotides bear a 5-phosphate group except oligonucleotide S2 which has the sequence permitting ligation immediately adjacent to the first oligonucleotide.

FIG. 9 depicts the results of a dot blot assay performed by the method of Example 1.

DETAILED DESCRIPTION OF THE INVENTION

Definitions

Figure 1:
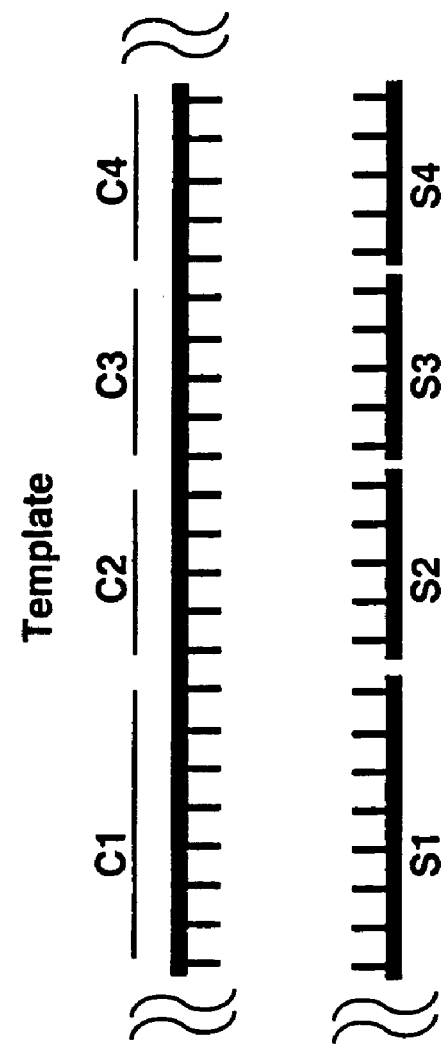
FIG. 1 depicts the juxtaposition of complementary oligonucleotides S1–S4 against a universal template having sequence regions C1–C4.
Figure 4:
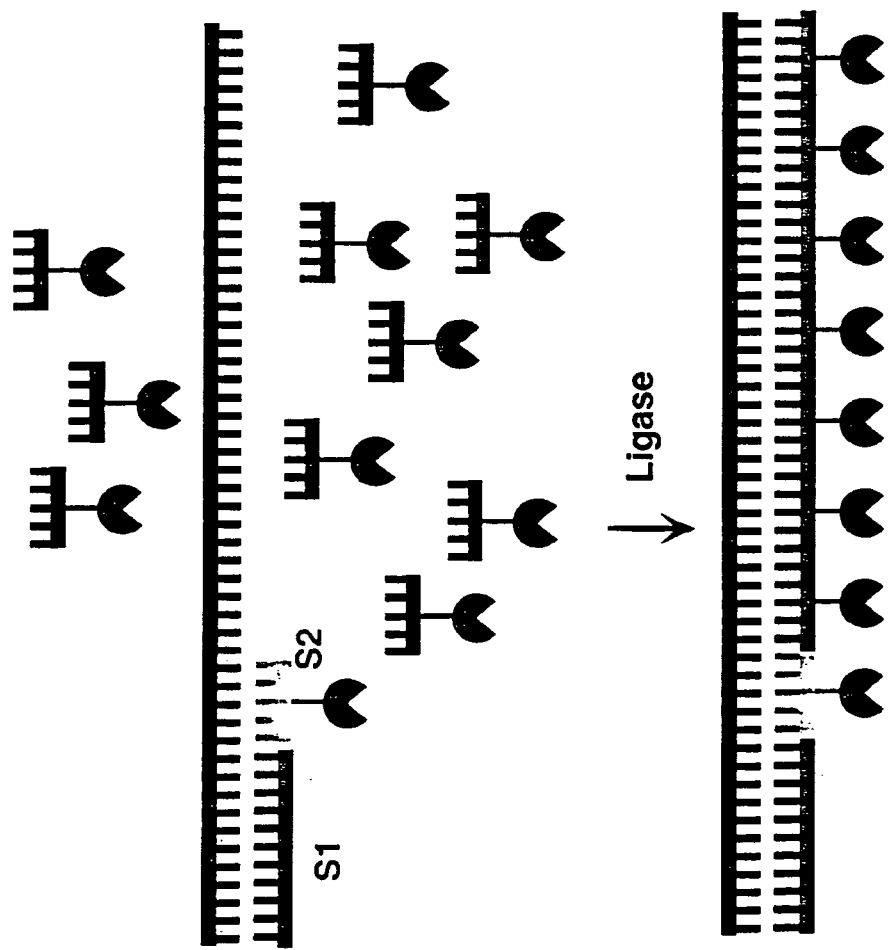
FIG. 4 depicts the subsequent ligation of the set of oligonucleotides which results only after the phosphorylation of oligonucleotide S2.
Figure 5:
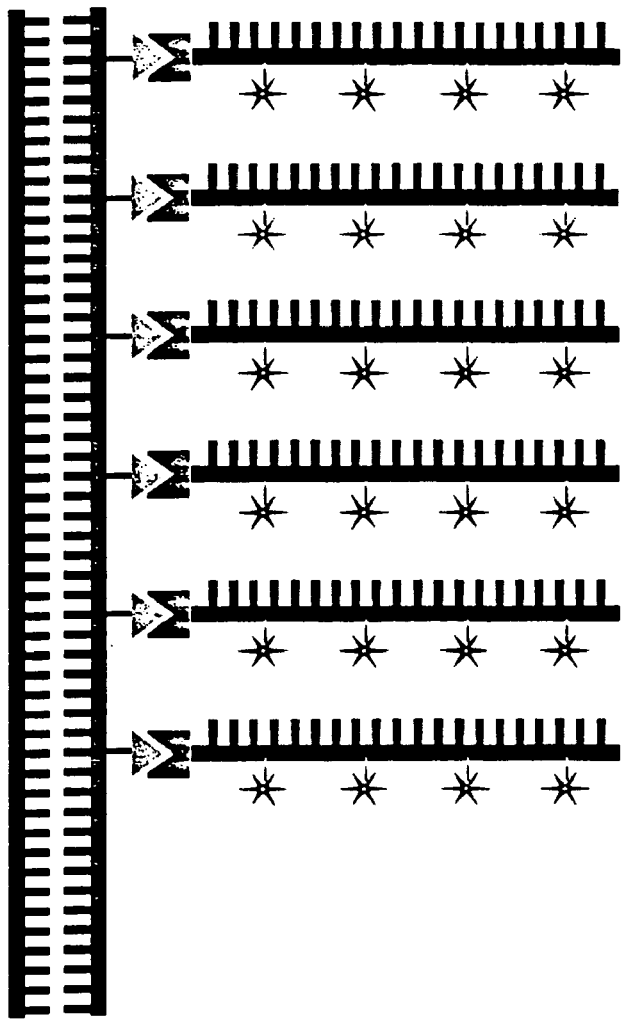
FIG. 5 depicts an embodiment where each oligonucleotide S2–Sn bears an affinity label which subsequently captures a multiply labeled signal oligonucleotide.
Figure 6:
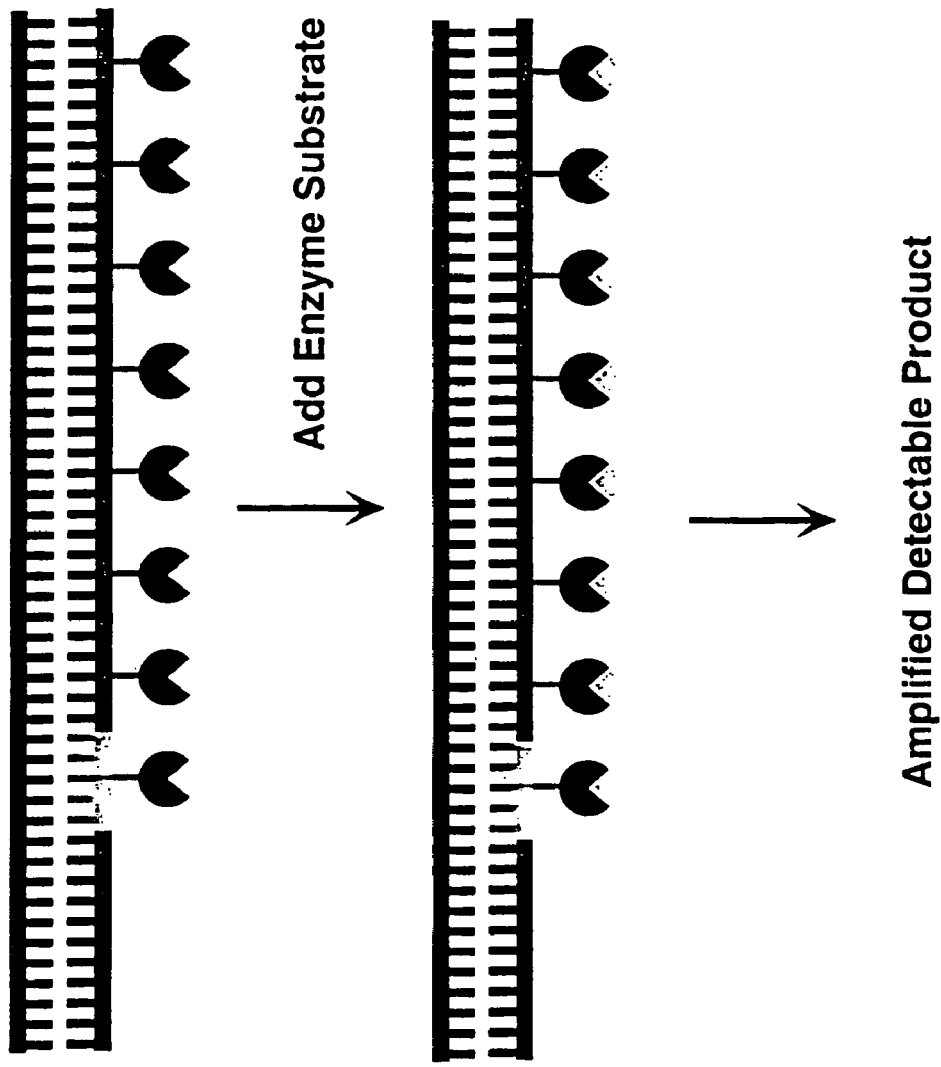
FIG. 6 depicts an embodiment where each oligonucleotide S2–Sn bears an enzyme label. The enzyme is detected by reaction with an enzyme substrate to form a detectable product.
Figure 7:
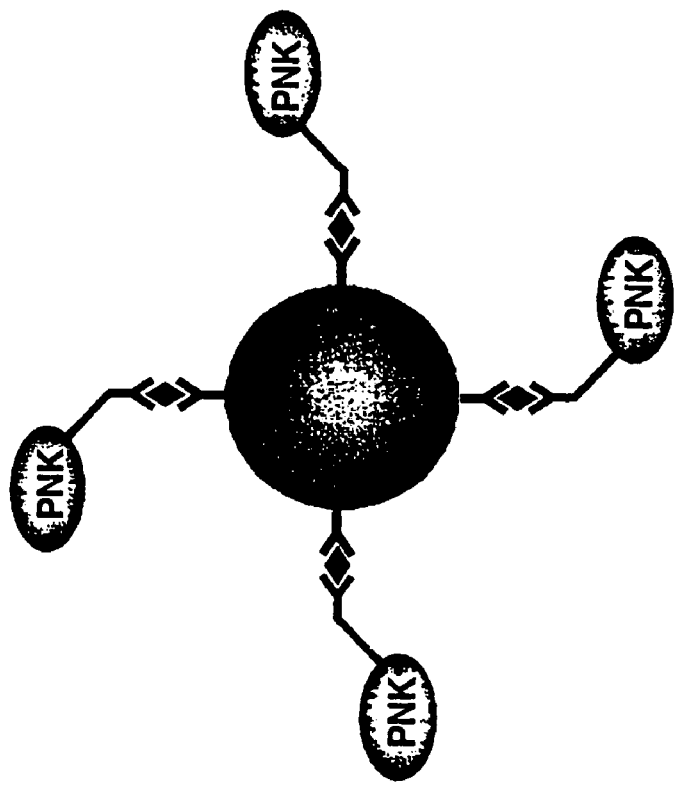
FIG. 7 depicts an assay format for performing a sandwich immunoassay using a PNK-labeled antibody.
Figure 8:
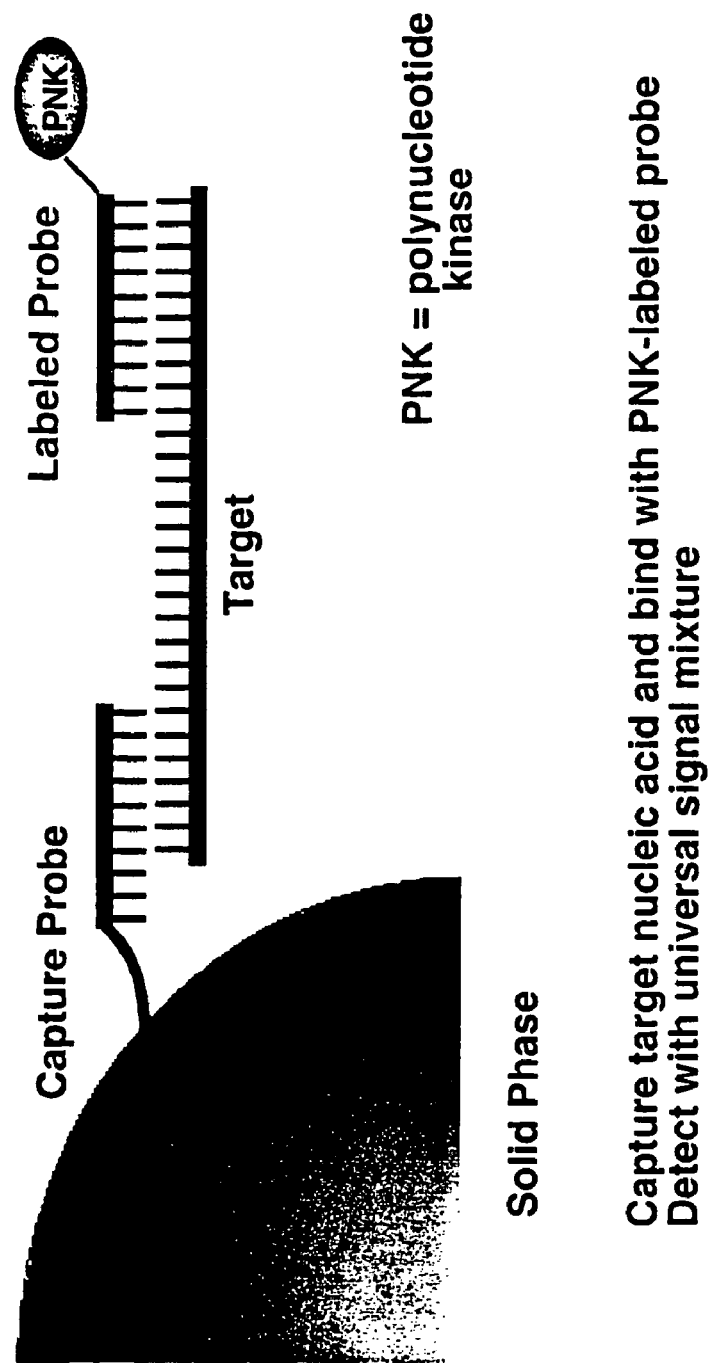
FIG. 8 depicts an assay format for performing a nucleic acid hybridization assay using a PNK-labeled probe.

Ligase—any enzyme, chemical or other species capable of catalytically effecting the covalent attachment of two oligonucleotides, polynucleotides or nucleic acids. The attachment is achieved by coupling the 5'-phosphate of one of the above species with a 3'-hydroxyl of another of the above species. Examples include RNA ligases, DNA ligases and ribozymes.

Oligomer, oligonucleotide—as used herein will refer to a compound containing a phosphodiester internucleotide linkage and a 5'-terminal monophosphate group. The nucleotides can be the normally occurring ribonucleotides A, C, G, and U or deoxyribonucleotides, dA, dC, dG and dT. The nucleotides can also be any of the known modified bases and degeneracy reducing or universal bases as long as they do not interfere with PNK or ligase activity.

First oligonucleotide—refers to an oligonucleotide used to direct the site of ligation and is required to initiate the ligation process. First oligonucleotides are of a length sufficient to hybridize stably to the template and preferably represent a unique sequence in the template. First oligonucleotides will usually be about 15–30 bases in length although longer sequences can be used. Labeled first oligonucleotides containing detectable labels or labels which allow solid phase capture are within the scope of the term as used herein. The term also contemplates contiguously stacked oligonucleotides of at least six bases as is known in the art (T. Kaczorowski and W. Szybalski, Gene, 179, 189–193 (1996)).

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like from human or animal specimens. Other types of samples include microbial cultures, plant material, food samples and environmental samples such as soil or water.

Short oligonucleotide—As used herein, a oligonucleotide 5'-phosphate of at least two and up to about 10 base length. The bases can be ribonucleotides or deoxyribonucleotides or analogs thereof. The length of a short oligonucleotide useful in a given context can vary within this range and may be less than the whole range. The preferred length varies depending on the particular application.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody and metal complex-ligand.

Template and target are used interchangeably and refer to the nucleic acid to which are hybridized the oligonucleotides undergoing ligation.

The present invention provides a new method of measuring the activity of PNK based on the phosphorylation of the 5'-OH of an oligonucleotide, polynucleotide or nucleic acid, having a sequence S2. The presence of the 5'-phosphate group permits ligation of the oligonucleotide, polynucleotide or nucleic acid onto another oligonucleotide, polynucleotide or nucleic acid, having a sequence S1, which is hybridized with a complementary oligonucleotide, polynucleotide or nucleic acid containing adjacent sequences C1 and C2 which are the complements or S1 and S2. In one embodiment, a set of n contiguous oligonucleotides having sequences S2–Sn are provided wherein the oligonucleotide having sequence S2 has a 5'-OH group, the oligonucleotides having sequence S3–Sn have a 5'-phosphate and the complementary oligonucleotide contains contiguous complementary sequences C1–Cn. Phosphorylation of the oligonucleotide having sequence S2 permits all of the oligonucleotides to be ligated together. In the absence of PNK, no phosphorylation occurs, therefore none of the oligonucleotides are ligated.

In one embodiment therefore there is provided a method comprising:
a) reacting polynucleotide kinase, a nucleotide triphosphate and an oligonucleotide having a 5'-OH group and comprising a sequence S2 to phosphorylate oligonucleotide S2 at the 5'-OH group;
b) providing a reaction mixture comprising
i) oligonucleotide S2,
ii) a single stranded nucleic acid template comprising contiguous sequence regions C1–Cn, wherein n is an integer greater than 2,
iii) a first oligonucleotide having a sequence S1 which is hybridized to region C1 of the template,
iv) a plurality of oligonucleotide 5'-phosphates having sequences S3–Sn, wherein each oligonucleotide 5'-phosphate is complementary to one region of the template C3–Cn, and
v) a ligase and a cofactor for the ligase; and
c) ligating with the ligase oligonucleotide S1 and oligonucleotide 5'-phosphate S2 and ligating at least one of the plurality of oligonucleotide 5'-phosphates S3–Sn in a contiguous manner onto oligonucleotide S2 to form a ligation product in one continuous process under conditions which do not permit stable hybridization of the oligonucleotides S2–Sn, wherein ligation of oligonucleotide 5'-monophosphates S2–Sn only occurs if oligonucleotide S2 is phosphorylated by polynucleotide kinase.

The oligonucleotide 5'-phosphates S3–Sn can be supplied for reaction in the phosphorylated form or they can be phosphorylated in situ. By the latter it is intended that oligonucleotides S3–Sn are supplied with 5-OH termini and phosphorylated by PNK under the reaction conditions. This mode would be advantageous if it were desired to incorporate a radioactive P atom in each interoligonucleotide linkage. Radiolabeled ATP would be used as the PNK cofactor.

In all embodiments of the present method in which a plurality of oligonucleotides is sequentially and contiguously ligated, the ligation reaction can proceed in either direction along the strand, i.e. from either the 5' or 3' end of the first oligonucleotide. The 5'-OH group of the first oligonucleotide must be phosphorylated when ligation is expected to proceed starting from the 5-terminus.

Oligonucleotide S1 can be supplied in 5'-phosphate form or 5'-OH form. When it is desired to perform multiple contiguous ligations proceeding from the 5'-end of S1, then S1 must contain a 5'-phosphate. Even when ligation will proceed from the 3'-end of S1, its 5' end may be phosphorylated so that its presence in a reaction mixture does not consume some of the phosphate source and divert PNK activity away from the desired phosphorylation of S2.

In another embodiment there is provided a method comprising:
a) reacting polynucleotide kinase, a nucleotide triphosphate and a plurality of oligonucleotides having sequences S2–Sn, each oligonucleotide having a 5'-OH group, to phosphorylate each oligonucleotide its 5'-OH group;
b) providing a reaction mixture comprising
i) oligonucleotide 5'-phosphates S2–Sn,
ii) a single stranded nucleic acid template comprising contiguous sequence regions C1–Cn, wherein n is an integer greater than 2, and wherein for each m which is an integer from 2-n, Sm is the complement of Cm,
iii) a first oligonucleotide having a sequence S1 which is hybridized to region C1 of the template,
iv) a ligase and a cofactor for the ligase; and
c) ligating with the ligase oligonucleotide S1 and oligonucleotide 5'-phosphate S2 and ligating at least one of the plurality of oligonucleotide 5'-phosphates S3–Sn in a contiguous manner onto oligonucleotide S2 to form a ligation product in one continuous process under conditions which do not permit stable hybridization of the oligonucleotides S2–Sn, wherein ligation of oligonucleotide 5'-monophosphates S2–Sn only occurs if oligonucleotide S2 is phosphorylated by polynucleotide kinase.

The polynucleotide kinase useful in the methods of the present invention is preferably T4 polynucleotide kinase (EC 3.7.1.78), an enzyme produced in T4 phage-infected *E. coli* having a molecular weight of 33 kDa. The enzyme can be produced by cloning and expression of the T4 gene pseT (C. A. Midgley, N. E. Murray, EMBO J., 4(10), 2695–2703 (1985); J. H. Kim, et al., Korean Biochem. J., 22(1), 26–32 (1989); M. Campos, et al., Gene, 101, 127–131 (1991)) and is commercially available. Ribozymes possessing PNK activity are known and are contemplated for use in the present methods as well. The use of PNK is typically performed in a buffer of pH between about 7 and 9 and requires a source of phosphate. Preferred sources are ATP, TTP, CTP and GTP with ATP being most preferred. Additional components beneficial for enzymatic activity are advantageously employed in phosphorylation reaction mixtures and include divalent metal ions such as $Mg^{+2}$, and thiol compounds including DTT and 2-mercaptoethanol.

The ligation component of the present methods uses a ligase such as a DNA ligase. Representative ligases include T4 ligase, T7 ligase, Tth ligase, Taq ligase and *E. coli* DNA ligase. The ligase can be a thermostable ligase, in which case thermal cycling techniques as discussed below are possible. Methods of performing enzymatic ligation reactions are generally described in e.g., Sambrook, et al., *Molecular Cloning: A Laboratory Manual,* 2nd Ed., Cold Spring Harbor Laboratory, New York, 1989.

Enzymatic ligation reactions are generally performed in a buffer solution, optionally in the presence of additives to promote hybridization. The buffer has a pH typically in the range of 6–9, preferably 7–8.5. The reaction can be performed over a range of temperatures in the range of 0 to about 50° C. Optimal temperatures will vary over the range depending on the nature and size of oligonucleotide phosphates to be ligated, the enzyme, presence and amount of additive and can be optimized empirically with reference to the general literature on ligases and by reference to the specific examples below. The length of time for performing the ligation can be as short as a few minutes up to several hours, although it is desirable to conduct the reaction as rapidly as possible. Single stranded DNA binding proteins can be added to oligonucleotide ligation reactions to improve their efficiency. Their effect is due to their relaxation of any secondary structure that is in the template strand thus allowing the complementary oligonucleotides to bind and ligate. *E. coli* single stranded binding protein (Promega, Madison, Wis. or Amersham/USB) and T4 Gene 32 protein (Boehringer Mannheim, Indianapolis, Ind.) can be used. The use of volume excluding agents such as polyethylene glycol (PEG) may be advantageous in promoting ligations. Inclusion of up to 200 mM NaCl may also be useful for promoting ligations. The use of other additives in enzymatic ligations is contemplated and is within the scope of the present methods. Additives include phosphate transfer agents such as ATP, sulfhydryl reagents, including DTT and 2-mercaptoethanol, and divalent cations such as $Mg^{+2}$ salts.

Template nucleic acid must be in or must be placed in single stranded form for annealing and hybridization of the first oligonucleotide and ligation of subsequent oligonucleotides. One manner in which single stranded template can be provided is by directly synthesizing single stranded nucleic acid. Alternately, the strands of double stranded nucleic acid can be separated using techniques and conditions known to one of skill in the art including thermal melting or use of chaotropic agents.

The creation of ligation product presents the means of assessing the activity, since no ligated product can form until the oligonucleotide having sequence S2 becomes phosphorylated. The ligated product can be detected by virtue of its length, by inclusion of a radioisotope such as a $^{32}P$ in the internucleotide bond. The latter would result from the use of $\gamma$-$^{32}P$ ATP in the phosphorylation reaction catalyzed by PNK. One or more of the oligonucleotides incorporated into the ligation product can bear a detectable label. In this case, detection of the presence of label signifies the success of ligation and therefore the occurrence of phosphorylation.

Detection of $^{32}P$-labeled ligated product can be accomplished by any suitable method known to one of ordinary skill in the art. These include scintillation counting and autoradiography using x-ray film. When none of the oligonucleotides used carries a detectable label, detection of the ligated product can be achieved by detecting an oligonucleotide product of the expected length or number of bases. This number will differ from and exceed that of any of the constituent oligonucleotides. Prior to or concurrently with the detection, the oligonucleotides can be separated by a suitable technique such as gel electrophoresis, high performance liquid chromatography or time-of-flight mass spectrometry. Gel-separated nucleic acids can be visualized with fluorescent intercalating dyes such as ethidium bromide and propidium bromide when in double stranded form. Chromatographic detection also requires no labeling and can be achieved by absorption spectrophotometry or refractive index.

The present methods are useful in their own right for detecting or measuring the activity of PNK. The methods could find use, for example, as a quality control measure for assaying the activity of commercial preparations of the enzyme. The methods are of further use when PNK is employed as a label to report the presence of a substance to be analyzed in an assay. In these embodiments PNK is covalently linked to a member of a specific binding pair such as an antibody, antigen or nucleic acid probe. The linkage may either be by direct conjugation or by means of secondary specific binding pairs. An example would be to use a primary specific binding partner for an analyte of interest which is labeled with biotin or a small hapten and a PNK-streptavidin or PNK-antibody conjugate.

When using the methods of the present invention wherein the PNK is provided as a label in an assay of an analyte in a sample, the amount of PNK detected by virtue of the subsequent phosphorylation-ligation reaction is correlated to the amount of analyte in the sample in the customary manner. As in all enzyme-coupled detection schemes, an amplification is expected since PNK functions catalytically to phosphorylate its substrate. This will be the case in the present methods provided that the phosphate donor, typically ATP, and an oligonucleotide with a 5'-OH are provided in large excess. The methods are capable of providing very high sensitivity because a second stage of signal amplification is imparted when multiple labeled oligonucleotides are ligated in the ligation step. Further, if the detectable label is an enzyme, a third stage of amplification will result as this label enzyme catalyzes formation of a detectable product. In this aspect, the method can be viewed as an enzyme cascade reaction scheme.

Methods of covalently coupling an enzyme to other molecules of biological interest are known to one of skill in the art. A reactive group on the enzyme is often used as the site of linkage, typically at an amino group in lysine side chains, or a sulfhydryl (—SH) group present in cysteine. Indirect labeling or linking can be achieved by using a secondary specific binding pair. As an example, PNK can be linked to an antibody or nucleic acid through the biotin-streptavidin interaction. One of the latter pair is linked to PNK using e.g. a biotin-NHS or biotin-maleimide derivative, while the other is conjugated to streptavidin. Other hapten/anti-hapten pairs can be used in place of the biotin/streptavidin pair. Examples include digoxigenin, fluorescein or p-nitrophenol with their respective antibodies. Other labeling methods are described in L. J. Kricka, *Ligand-Binder Assays*, Marcel Dekker, Inc., New York, 1985, Chapter 2, pp. 15–51. Representative methods of labeling nucleic acids are described in C. A. Dangler, *Nucleic Acid Analysis*, Wiley-Liss., New York, 1996, Chapter 3, pp. 47–66.

Bifunctional coupling reagents can also be used to couple labels to organic and biological molecules with moderately reactive groups (see L. J. Kricka, *Ligand-Binder Assays*, Marcel Dekker, Inc., New York, 1985, pp. 18–20, Table 2.2 and T. H Ji, "Bifunctional Reagents," *Methods in Enzymology*, 91, 580–609 (1983)). Included are two types of bifunctional reagents, those which become incorporated into the final structure and those which do not and serve only to couple the two reactants.

Another object of the invention is a method for detecting an analyte comprising:

a) performing a specific binding pair reaction for detecting the analyte wherein polynucleotide kinase is present as a label on a specific binding pair member;

b) reacting polynucleotide kinase, a nucleotide triphosphate and an oligonucleotide having a 5'-OH group and comprising a sequence S2 to phosphorylate oligonucleotide S2 at the 5'-OH group;

c) providing a reaction mixture comprising
  i) oligonucleotide S2,
  ii) a single stranded nucleic acid template comprising contiguous sequence regions C1 and C2,
  iii) a first oligonucleotide having a sequence S1 which is hybridized to region C1 of the template, and
  v) a ligase and a cofactor for the ligase;

d) ligating with the ligase oligonucleotide S1 and oligonucleotide 5'-phosphate S2 to form a ligation product, wherein the ligation only occurs if oligonucleotide S2 is phosphorylated by polynucleotide kinase;

e) detecting the ligated oligonucleotide product of step d as indicating the presence or activity of the polynucleotide kinase; and f) relating the activity of the polynucleotide kinase to the amount of the analyte.

In another embodiment, there is provided a method for detecting an analyte comprising:

a) performing a specific binding pair reaction for detecting the analyte wherein polynucleotide kinase is present as a label on a specific binding pair member;

b) reacting polynucleotide kinase, a nucleotide triphosphate and an oligonucleotide having a 5'-OH group and comprising a sequence S2 to phosphorylate oligonucleotide S2 at the 5'-OH group;

c) providing a reaction mixture comprising
i) oligonucleotide S2,
ii) a single stranded nucleic acid template comprising contiguous sequence regions C1–Cn, wherein n is an integer greater than 2,
iii) a first oligonucleotide having a sequence S1 which is hybridized to region C1 of the template,
iv) at least one additional oligonucleotide 5'-phosphate having a sequence complementary to a region of the template, wherein the additional oligonucleotide 5'-phosphates are selected to be complementary to contiguous regions of the template C3–Cn, and
v) a ligase and a cofactor for the ligase;

d) ligating with the ligase oligonucleotide S1 and oligonucleotide 5'-phosphate S2 and ligating at least one of the plurality of oligonucleotide 5'-phosphates S3–Sn in a contiguous manner onto oligonucleotide S2 to form a ligation product in one continuous process under conditions which do not permit stable hybridization of the oligonucleotides S2–Sn, wherein ligation of oligonucleotide 5'-monophosphates S2–Sn only occurs if oligonucleotide S2 is phosphorylated by polynucleotide kinase;

e) detecting the ligated oligonucleotides of step d as indicating the presence or activity of the polynucleotide kinase; and f) relating the activity of the polynucleotide kinase to the amount of the analyte.

In another embodiment, there is provided a method for detecting an analyte comprising:

a) performing a specific binding pair reaction for detecting the analyte wherein polynucleotide kinase is present as a label on a specific binding pair member;

b) reacting polynucleotide kinase, a nucleotide triphosphate and an oligonucleotide having a 5'-OH group and comprising a sequence S2 to phosphorylate oligonucleotide S2 at the 5'-OH group;

c) providing a reaction mixture comprising
i) oligonucleotide S2,
ii) a single stranded nucleic acid template comprising contiguous sequence regions C1–Cn, wherein n is an integer greater than 2,
iii) a first oligonucleotide having a sequence S1 which is hybridized to region C1 of the template,
iv) a plurality of oligonucleotide 5'-phosphates having sequences S3–Sn, wherein each oligonucleotide 5'-phosphate is complementary to one region of the template C3–Cn, and
v) a ligase and a cofactor for the ligase;

d) ligating with the ligase oligonucleotide S1 and oligonucleotide 5'-phosphate S2 and ligating at least one of the plurality of oligonucleotide 5'-phosphates S3–Sn in a contiguous manner onto oligonucleotide S2 to form a ligation product in one continuous process under conditions which do not permit stable hybridization of the oligonucleotides S2–Sn, wherein ligation of oligonucleotide 5'-monophosphates S2–Sn only occurs if oligonucleotide S2 is phosphorylated by polynucleotide kinase;

e) detecting the ligated oligonucleotides of step d as indicating the presence or activity of the polynucleotide kinase; and f) relating the activity of the polynucleotide kinase to the amount of the analyte.

In one embodiment, the template/first oligonucleotide hybrid is immobilized or covalently linked to a solid support. The linking can be either prior to, during or after the ligation of additional oligonucleotides onto the hybridized first oligonucleotide. The solid phase is preferably not the same solid phase, if one is used, to which the PNK-labeled analyte binding reagent is immobilized. A preferred solid phase for immobilizing the template/oligonucleotide hybrid comprises magnetic particles. Use of magnetic particles facilitates removal of unreacted reaction components whose presence would interfere with product detection.

A preferred format for performing an assay in accordance with the methods of the present invention comprises using a PNK-labeled specific binding partner for an analyte wherein the PNK-labeled specific binding partner is immobilized directly or indirectly on a solid phase prior to, during or after a specific binding reaction with the analyte. PNK label not specifically associated with the analyte is removed. A reaction mixture comprising a phosphate donor such as ATP and at least one oligonucleotide having a 5'-OH group is reacted with the PNK-labeled specific binding pair in a solution. The solution is removed from the immobilized PNK and added to a second reaction mixture comprising a template/first oligonucleotide hybrid, a ligase, a co-factor for the ligase and, if desired, additional oligonucleotides having a 5'-phosphate. The additional oligonucleotide 5-phosphates will have sequences which permit them to be ligated contiguously to the ligated first and second oligonucleotides. A ligation product is formed which is then detected on the basis of its length, the incorporation of $^{32}P$ or the presence of labels.

Advantageously, the template, and all oligonucleotides used in phosphorylation and ligation can be of any convenient sequence. A further advantage is that since the template and set of oligonucleotides are only used as a detection or reporter system and are not involved in the initial binding reaction involving the analyte, one template and set of oligonucleotides can be used universally in any assay or can be used as a universal reporter system in a multi-analyte detection instrument.

The length of oligonucleotides to use in the present methods is governed by several factors. In embodiments wherein only one oligonucleotide is required to be ligated to the hybridized first oligonucleotide, length is not critical. Any convenient length oligonucleotide can be used as long as it is capable of being ligated. It is not necessary that it be stably hybridized to the template prior to ligation. In embodiments wherein a plurality of oligonucleotides is to be sequentially ligated, it is preferred that each oligonucleotide in the plurality be of a length that is smaller than that of the first (hybridized) oligonucleotide. Ligation is performed by setting conditions which do not permit the plurality of oligonucleotides to stably hybridize to the template. The second and subsequent oligonucleotides will only be incorporated into the template-bound ligated product strand through the ligation process. In this manner the best discrimination of results is obtained. In practice, a difference in base length between the hybridized first and subsequent oligonucleotides of at least about five bases is desirable. In this manner the best discrimination of results is obtained.

Shorter oligonucleotides are advantageous in some embodiments since they are easier to prepare, they require less compounds to construct an entire library and their use allows more detectable labels to be incorporated into the ligated product. On the other hand they become more difficult, e.g. lower temperature, to ligate as their length decreases. This, in turn, translates to greater stringency at a given temperature. Longer oligonucleotides have the ability to hybridize and initiate ligation at a site not associated with the first oligonucleotide. This has been demonstrated to occur, under the right conditions, with oligonucleotides as small as 6 bases (T. Kaczorowski and W. Szybalski, Gene, 179, 189–193 (1996); L. E. Kotler, D. Zevin-Sonkin, I. A. Sobolev, A. D. Beskin and L. E. Ulanovsky, Proc. Natl. Acad. Sci. USA, 90, 4241–4245 (1993)). Ligation of 2 or more contiguous hexamers to produce e.g., a dodecamer or octadecamer, then effectively produces a new ligation start point. If this happens, the ability to control the starting point for polynucleotide synthesis is compromised. Such ligation in the absence of the first oligonucleotide is undesirable in the present methods and must be avoided.

The size of the oligonucleotides to be used in the multiple ligation embodiments can take any convenient value, typically from 2 to about 20 bases. More usually, oligonucleotides of about 4 to 12 bases are used and preferably from 5 to 8 bases. The first oligonucleotide which is hybridized to the template and directs the start of ligation is preferably at least about 10 bases and can have any practical length. Preferred oligonucleotides in this regard will be from about 15–30 bases.

In those embodiments wherein a series of short oligonucleotides is simultaneously ligated onto a template-bound first oligonucleotide in a contiguous manner to produce a complementary strand of a template, the complementary strand so produced can be either labeled or unlabeled by using either labeled or unlabeled short oligonucleotides. The oligonucleotides in the set can each contain the same number of bases or different numbers of bases. When a sequence of the template is known exactly, a set containing the minimum number of oligonucleotides can be used. The oligonucleotides are ligated in the correct order starting from the first oligonucleotide to produce the correct sequence. Templates having variable sequence regions can also be used. Oligonucleotides corresponding to the variable sequence region and which collectively contain all the possible sequence variations are supplied and reacted in the manner described in the present methods.

It is not necessary in the present methods, except as explicitly noted below, that each component of the set of oligonucleotide 5'-phosphates used in a given method be of the same number of bases. It can be advantageous in some embodiments to use a combination of oligonucleotides of two or more different lengths, such as pentamers and hexamers.

In another embodiment, template-directed ligation of a plurality of a set of short oligonucleotides of the same length onto a first, hybridized, oligonucleotide can be performed in a manner which controls the endpoint of the ligation by the use of nonextendable oligonucleotides. A nonextendable oligomer can contain the same or a different number of bases as the other oligonucleotides in the set. The nonextendable oligomer contains a 5'-phosphate so that it can be ligated, but lacks the 3'-OH group. It could, for example, have a dideoxy base at the 3'-end of the oligomer so that there is no 3'-OH for ligation. Another type of nonextendable oligomer contains a blocked 3'-OH group for example where the hydroxyl group is blocked with a methyl group or a phosphate group, to prevent subsequent ligation. Modifications to the terminal base which prevent ligation are another possible type of nonextendable oligomer. The nonextendable oligomer can be labeled or unlabeled, depending on the need. A preferred embodiment is to use oligonucleotides containing a dideoxy base at the 3'-terminus.

In a preferred embodiment, some or all of the oligonucleotides to be ligated are detectably labeled. The label borne on each oligonucleotide can be different or all can be the same label. Alternately, a limited number of different labels, e.g. 2–5 labels, can be employed. The choice of labels used will be governed by the final application. The labels can be virtually detectable species, including radioisotopes, mass tags, metal particles, enzymes, chemiluminescent labels, fluorescent labels, or calorimetric labels detected on the basis of absorption of light.

Label also encompasses compounds useful for attaching or binding other detectable species. Included in this type of labeling group are specific binding molecules including antigens and antibodies, binding proteins such as streptavidin and haptens such as biotin and digoxigenin. When the label is a small hapten, the detectable label can be a species such as an enzyme which is bound to the nucleic acid via an enzyme-anti-hapten conjugate. In the latter regard, the use of multiple oligonucleotide ligation provides still another advantage. Optimum spacing between bulky enzyme labels can be achieved, e.g. by attachment at every fifth base, which places them at nearly 180° angles along the double helix from the nearest neighboring label.

The detectable label can also be a polymeric label which contains multiple detectable species. Preferred polymers are nucleic acids and polypeptides. The labels can be linear polymers, branched polymers or dendrimeric compounds. In practice, some or all of the oligonucleotides would comprise a "handle" such as a hapten or short recognition sequence which is used to bind to a multiply labeled polymer.

Detectable labels can be detected in any of several ways. Enzyme labels are preferred because of their ability to catalyze the formation of large amounts of detectable product. Enzymes useful as detectable labels include, without limitation, phosphatases, other hydrolases including esterases, galactosidase, glucosidase or glucuronidase, urease, luciferases, peptidases and proteases, oxidase enzymes such as glucose oxidase or xanthine oxidase, and peroxidase enzymes such as horseradish peroxidase, microperoxidase or lactoperoxidase. Preferred enzymes in this regard include alkaline phosphatase, β-galactosidase, β-glucuronidase, glucose oxidase and horseradish peroxidase.

Substrates for the enzymes serving as the detectable label include any of the compounds known to the skilled artisan which produce a colored product, a fluorescent product or chemiluminescence or bioluminescence. A variety of such substrates are in widespread commercial use. One skilled in the art can readily identify suitable substrates by consultation of the primary scientific and patent literature, reviews and trade information. A representative listing by way of illustration only includes p-nitrophenyl phosphate, BCIP, umbelliferone phosphate, dioxetane phosphates and acridan phosphates for reaction with alkaline phosphatase, X-gal, umbelliferone galactoside and dioxetane galactoside compounds for reaction with β-galactosidase; TMB, ABTS, luminol and acridan esters for reaction with horseradish peroxidase. Furthermore, the use of enzyme cascade or enzyme cycling schemes are known for increasing the sensitivity of detecting enzymes. In this format, an enzyme produces a cofactor for another enzyme or converts another enzyme into a catalytically active form. Excellent detection sensitivity can result from use of this type of detection. An exemplary enzyme cycling reaction uses alkaline phosphatase to produce NADH from NADPH. The NADH enters into a cyclic reaction with alcohol dehydrogenase reducing ethanol and diaphorase oxidizing a colorless substrate to a colored formazan product (A. Johannson, D. L. Bates, J. Immunol. Meth., 87, 7–11 (1986)).

In another embodiment, the detectable label is a fluorescent molecule such as the fluorescers FAM, JOE, ROX and TAMRA commonly used in automated dideoxy sequencing. Numerous methods of labeling nucleotides and oligonucleotides are known in the art and include direct attachment of label (Haugland, *Handbook of Fluorescent Probes and Research Chemicals*, (Molecular Probes, Eugene, Oreg.), 1992). Labeling can also be accomplished by indirect means where, for example, where a universal linker such as biotin is provided as the primary label and a fluorescer-labeled binding partner for biotin provides the label.

In another embodiment, the label is a chemiluminescent compound and the quantity of label is detected by the light intensity produced by triggering the generation of chemiluminescence from the label. Several types of chemiluminescent compounds are known and can be used as labels. Representative examples include acridinium esters and sulfonamides, luminol or isoluminol derivatives, and dioxetanes. Chemiluminescent compounds and labels are described in R. Handley, H. Akhavan-Tafti, A. P. Schaap, J. Clin. Ligand Assay, 20(4) 302–312 (1997). A preferred chemiluminescent label is an acridan phosphate compound as disclosed in Applicant's co-pending application Ser. No. 09/099,656. The latter compounds are used advantageously because of their stability, high chemiluminescence quantum efficiency, ease of conjugation and ability to be triggered under a wide range of conditions, including in electrophoresis gels. Bioluminescent and electrochemiluminescent compounds are considered within the scope of detectable chemiluminescent labels.

In another embodiment, the label is a chromogenic compound and the quantity of label is detected by light absorbance. Another label type is a radioisotope such as $^{32}P$, $^{33}P$ and $^{35}S$ whose presence can be detected using scintillation counting or x-ray imaging. The label can also be an enzyme such as alkaline phosphatase, β-galactosidase, luciferase and horseradish peroxidase. The quantity of enzyme is determined by measuring the action of the enzyme on a fluorogenic, chromogenic or chemiluminogenic substrate.

Yet another embodiment comprises providing a suitable fluorescent donor as a label on the first oligonucleotide and a suitable fluorescent acceptor or fluorescence quencher as a label on the subsequent oligonucleotides. It is not necessary to label each oligomer. Ligation is performed on hybridized first oligonucleotide to form an extended ligation product bearing a fluorescent donor and one or more fluorescent acceptor labels. Under suitable conditions, i.e. when the donor and acceptor possess sufficient spectral overlap for energy transfer to be feasible and the spatial separation between donor and acceptors are within the Förster distance, energy transfer between fluorescers or between fluorescer and quencher can occur within the extended ligation product. Irradiation of the ligated product at a wavelength absorbed by the fluorescent donor results in fluorescence from the acceptor or in quenching.

Another method for detecting a target nucleic acid based on the ligation of a plurality of labeled oligonucleotides comprises using a fluorescent intercalating dye as a label. It is known that certain dyes become fluorescent when intercalated within the double helix of double stranded nucleic acids. An example is the widely used compound ethidium bromide. As an optional step, agarose can be added to the reaction to enhance fluorescence.

The fraction of labeled oligonucleotides to use can be selected empirically with regard to the desired degree of detection sensitivity by using a range of different label densities. It may be desirable, depending on the size of the oligonucleotide 5'-phosphates, to limit the fraction of labeled oligonucleotides to avoid self quenching of fluorescence.

Methods performed in accordance with the present invention which use polynucleotide kinase as a label are generally useful in many types of diagnostic applications based on immunological binding reactions or nucleic acid hybridization interactions. One embodiment comprises an enzyme-linked immunoassay using PNK as the enzyme. In this type of assay, a PNK is conjugated to one member of a specific binding pair. An example is the so-called enzyme-linked immunosorbent assay or ELISA. Such assays are commonly used in manual format as well as on automated multi-test immunoassay systems. In a typical immunoassay, the analyte hapten, antigen or antibody is assayed by detecting the presence or amount of an enzyme-labeled specific binding partner for the analyte or an enzyme-labeled analog of the analyte. Various assay formats and the protocols for performing the immunochemical steps are well known in the art. These assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies with the analyte, one of which is labeled with PNK. The PNK-labeled binding pair so formed is assayed by the methods of the present invention. When the label is a member of another specific binding pair, e.g. a hapten, a conjugate of its binding partner with PNK is bound to it and the PNK then detected in accordance with the present methods. Measurement can be performed with enzyme-labeled species attached to a solid surface or support including beads, tubes, microwells, magnetic particles, test strips, membranes and filters such as are in common use in the art. The PNK-labeled species can also be present free in solution or enclosed within an organized assembly such as a liposome in which case a lytic agent is employed to lyse the liposome and free the detectable enzyme.

In addition to the aforementioned antigen-antibody, hapten-antibody or antibody-antibody pairs, specific binding pairs also can include complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

A particularly useful application of the present detection methods is the detection of nucleic acids by the use of a PNK-labeled nucleic acid probe. In these methods at least one probe having a sequence specific for the nucleic acid analyte of interest is used. In one commonly used format a first probe immobilized to a solid support, termed a capture probe, is used to hybridize with the target sequence. Then a second probe complementary to the target and bearing the PNK label is hybridized. Other methods and test formats for analysis and detection of nucleic acids using enzyme-labels, for example, solution hybridization assays, DNA detection in Southern blotting, RNA by Northern blotting, DNA sequencing, DNA fingerprinting, colony hybridizations and plaque lifts are all well established techniques. The PNK label can be present as a direct conjugate with a probe oligonucleotide or capture oligonucleotide or it can be incorporated through the indirect linking means identified above in connection with immunoassays. Such nucleic acid assays can be performed on a blotting membrane or in solution using oligonucleotides attached to solid surfaces including beads, tubes, microwells, magnetic particles or test strips such as are known in the art.

Such methods have use in many areas of nucleic acid diagnostics, including detection of infectious agents such as C. trachomatis and N. gonorrhoeae, P. carinii, M. tuberculosis, detection of food borne pathogens such as Salmonella and E. coli, methods of detecting the expression of genes in high throughput screening assays by detecting either RNA or cDNA, methods of detecting genetic abnormalities, forensic testing of DNA samples from suspected criminals, identity matching of human remains and paternity testing.

In the area of genetic abnormality testing, one application is a method for the detection of genetic mutations. The mutations can be a point mutation (a and β-Thalassemia), a single base substitution (Sickle Cell Anemia), a deletion (Cystic Fibrosis $\Delta F_{508}$, Tay-Sachs), an insertion, a duplication, a transposition of bases or a combination of the above. Capture probes comprising a sequence specific for one state of the mutation are used to distinguish among the different genotypes present in a sample.

In order to more fully describe various aspects of the present invention, the following representative examples are presented are presented for the purpose of illustrating typical experimental procedures and conditions. Variations of the exemplary conditions and variables known to those of skill in the art and contained in standard treatises can be made without departing from the spirit or scope of the present invention.

EXAMPLES

Example 1

The effectiveness of the present methods was assessed in a dot blot hybridization format assay of PNK activity using serial dilutions of a PNK stock solution. An octamer, VC-19, having the sequence 5'-TCCGGTAA was phosphorylated with PNK and ligated to a 20-mer, VC-3, hybridized to pUC 18 template DNA. The template was a 285 bp PCR product from positions 2174–2458 of the plasmid sequence (WO88/09373, Dec. 1, 1988). The 20-mer VC-3 has the sequence: 5'-GGGAGAAAGGCGGACAGGTA (Seq. ID#1).

a. Dilution of PNK:

Procedure: 1 μL of PNK (30 U/μL) diluted to 21 μL with PNK dilution buffer to yield a concentration of 1.428 U/μL. This solution was again diluted 1 μL in 20 μL reaction to yield a first dilution having a concentration of 0.071 U/μL. Additional 10-fold dilutions were prepared. The final solutions had PNK concentrations:

Dilution 1 $7\times10^{-2}$ U/μL

Dilution 2 $7\times10^{-3}$ U/μL

Dilution 3 $7\times10^{-4}$ U/μL

Dilution 4 $7\times10^{-5}$ U/μL

Dilution 5 $7\times10^{-6}$ U/ML

Dilution 6 0 U (control)

b. Ligation Reactions:

Each ligation reaction was run in duplicate. Each tube (1–6) contains: 5 μL of a ~400 ng/μL pUC 18 template (PCR column purified); 1 μL of VC-3 20-mer; 5 μL of VC-19 octamer; 5 μL of H$_2$O, in a total volume of 16 μL. The template/20-mer/octamer mixtures were allowed to react at 94° C. for 5 min, 65° C. for 2 min, and 20° C. for 2 min, then all 12 tubes were spun briefly. Then 2 μL of 10× T4 DNA ligase buffer (66 mM Tris HCl, pH 7.6, 6.6 mM MgCl$_2$, 10 mM DTT, 66 μM ATP, Amersham) was added to each tube, followed by 1 μL of PNK from each dilution and 1 μL T4 DNA ligase (1:10 dilution in T4 DNA ligase buffer). Each solution was gently mixed, spun and incubated at 20° C. for 4 h 40 min.

c. Dot Blots:

An 8 cm×7.5 cm piece of positively charged nylon membrane (Boehringer-Mannheim, Indianapolis, Ind.) was partitioned into 6 portions via pencil lines. Each portion was spotted in duplicate with 1 μL of pUC 285 template (ca. 400 ng) and air dried for 10 min. The blots were denatured for 3 min on a 3 mm Whatman paper (2 pieces) soaked in denaturing buffer. The blots were then moved to another 3 mm Whatman paper soaked in neutralizing buffer for 2 min, and this step was repeated for another 2 min. The blots were placed on 2×SSC paper for 2–3 min, and then UV-crosslinked by placing on a wet Whatman paper in 2×SSC. The blots were air-dried and stored at 25° C. overnight.

The dot blot was cut into 6 pieces and each piece was separately wet with 6×SSC for 5–8 min, and incubated in 5 mL Dig EasyHyb™ buffer (Boehringer-Mannheim) at 45° C. for 1 h with slow rocking (pre-hybridization).

d. Purification of Ligation Product:

Each ligation reaction buffer was taken in 5 volumes of PB buffer (Qiagen, Santa Clarita, Calif.) (22 μL reaction volume→110 μL buffer volume) and purified on a PCR purification column (QIAquick PCR purification kit, Qiagen). The purified probes were collected from the columns and used in the hybridization described below.

e. Hybridization:

Each set of probes was mixed separately with 4 mL of Dig Easy Hyb buffer at 45° C. The pre-hybridization buffer from step c was removed by aspiration, and the probes were added separately to dishes containing one of the previously prepared dot blots. The dishes were incubated for 3 h at 45° C. with rocking.

f. Washes:

The hybridization solutions from step e were removed by aspiration, and the blots washed sequentially as detailed below. All wash buffers were prewarmed to 55° C. for 2 h.

1×2 min in 3.5×SSC/0.1% SDS at 55° C.

1×15 min in 3.5×SSC/0.1% SDS, 50 mL/dish

2×15 min in 0.5×SSC/0.1% SDS at 55° C., 50 mL/dish

2×5 min in 2×SSC at 25° C., 5 mL/blot

1×5 min in 0.1 M maleic acid buffer, 0.15 M NaCl, pH 7.5,

Each wash used 5 mL/blot.

g. Detection:

The blots were blocked for 30 min in 2% Boehringer-Mannheim blocking buffer, then incubated for 30 min in a 1:10,000 dilution of anti-biotin-HRP (Boehringer-Mannheim) in 2% block, followed by two 15 min washes in 0.3% Tween-20/maleic acid buffer. HRP activity was measured by briefly incubating the blots in a solution of Lumigen® PS-3 (Lumigen, Southfield, Mich.) for 3 min, draining excess reagent and exposing the blots to x-ray film for 5 min. The blots probed with ligation product formed in the reactions using from $7 \times 10^{-2}$ U to $7 \times 10^{-5}$ U of PNK (5.3 fmol –5.3 amol) were distinguishable from a blank run without PNK.

This method presents a very conservative method of assessing detection sensitivity of PNK for a number of reasons. Autoradiography is known not to be the most sensitive means for detection of visible light, particularly in view of the known reciprocity of such film in which a threshold intensity must be reached before any signal registers on the film. The probe (ligation product) purification in step d almost certainly does not recover all of the product. The hybridization step e involves an inefficient use of the ligated product in preparing a dilute solution of the ligated product for hybridization to the template spots. Finally the antibody-HRP binding in the last step also entails some loss of efficiency.

Example 2

In this example, a set of pentamers was sequentially ligated to a 26-mer first oligonucleotide after reaction of the first pentamer with PNK. All other pentamers were provided as the 5'-phosphates. The template was a PCR amplified product (192 bp, 1525–1716 of GenBank sequence) of exon 10 region of the cystic fibrosis transmembrane regulator (CFTR) gene (J. R. Riordan, et al, Science, 245, 1066–1073 (1989)). Pentamers and 26-mer bearing a 5'-phosphate group were obtained commercially (Oligos Etc., Wilsonville, Oreg.). The base sequence of the 26-mer, designated GE-1, is:

5'-PO$_4$-AGTGGAAGAATTTCATTCTGTTCTCA. (SEQ. ID #2)

A Southern blot hybridization format assay with chemiluminescent detection was used to assess PNK activity.

Procedure:

a. Dilution of PNK:

Serial ten-fold dilutions of a PNK stock solution (30 U/μL) were prepared. The dilutions had PNK concentrations:

Dilution 1 3 U/μL

Dilution 2 $3 \times 10^{-1}$ U/μL

Dilution 3 $3 \times 10^{-2}$ U/μL

Dilution 4 $3 \times 10^{-3}$ U/μL

Dilution 5 $3 \times 10^{-4}$ U/μL

Dilution 6 $3 \times 10^{-5}$ U/μL b. Sample Preparation:

A stock mixture containing 21 μL of CFTR PCR product (~150 ng/μL), 7 μL phosphorylated GE-1 26-mer (100 ng/μL), 7 μL of each of the following pentamers (20 ng/μL): FS-1 (5' HO-GTTTT), NE-3-biotinylated (5' PO$_4$-CGTGG, T is biotinylated), NE-4 (5' PO$_4$-ATTAT), NE-5-biotinylated (5' PO$_4$-GCCTG, T is biotinylated), NE-6 (5' PO$_4$-GCACC), NE-7-biotinylated (5' PO$_4$-ATTAA, A at 3'-end is biotinylated), and 49 μL of deionized water was made up and then aliquotted into 17 μL samples A through G. Sample G was used as a negative control. A positive control designated Sample H contained 3 μL of template, 1 μL of GE-1 first oligonucleotide, 1 μL of NE-2 (5' PO$_4$-GTTTT in place of the FS-1 5'-OH pentamer), 1 μL of each of the following pentamers: NE-3-biotinylated, NE-4, NE-5-biotinylated, NE-6, NE-7-biotinylated, and 7 μL of deionized water.

c. Ligation Reactions:

The samples were maintained at 94° C. for 5 min, 65° C. for 2 min, and 16° C. for 2 min. Then 2 μL of T4 DNA ligase buffer was added to each of the samples. A 1 μL aliquot of PNK dilutions 1–6 were added to Samples A–F, respectively and 1 μL of T4 DNA ligase (Amersham) was added to each sample as a 1:10 dilution in the T4 DNA ligase buffer. The samples were allowed to react at 16° C. for 4 h. Then one-half the volume of the reaction mixture was removed, and the remaining reaction mixture was allowed to react overnight at 16° C.

d. Southern Blotting:

Both the 4 h ligation samples and the overnight ligation samples were separated on two PAGE-Urea gels (8% acrylamide, 7 M urea in 89 mM Tris-borate, 2 mM EDTA) (Amersham Pharmacia Biotech, Piscataway, N.J.), semi-dry blotted and UV-crosslinked.

e. Detection:

The blots were blocked in 2% Boehringer-Mannheim blocking buffer, then incubated with anti-biotin-alkaline phosphatase conjugate (Boehringer-Mannheim) for 30 min in 2% block (Boehringer-Mannheim), followed by two 15 min washes in 0.3% Tween-20/0.1 M maleic acid buffer, 0.1 M NaCl, pH 7.5. AP activity was measured by briefly incubating the blots in a solution of Lumi-Phos® Plus (Lumigen), draining excess reagent and exposing the blots to x-ray film. The blots probed with ligation product formed in the reactions using Samples A–F containing 3 U to $3 \times 10^{-5}$ U of PNK were distinguishable from a blank run without PNK after 13 min with a 1 min exposure.

Example 3

An experiment performed in accordance with the methods of Example 2 can also be performed in a two step manner by separately performing the PNK phosphorylation and ligation steps. In this variation, the first pentamer which contains a 5'-OH is separately reacted with PNK in T4 DNA ligase buffer containing ATP for 2 h at a suitable temperature, e.g. 16° C.–37° C. Subsequently, the reaction solution is mixed with the remaining pentamers, the ligase and ligase buffer and ligation performed as described above.

Example 4

In this example, a 19-mer was phosphorylated with PNK and ligated to a 26-mer first oligonucleotide after reaction of the first pentamer with PNK. A Southern blot hybridization format assay with chemiluminescent detection was used to assess PNK activity.

Procedure:

a. PNK Dilution:

The PNK dilutions were as follows: Sample 1: 3 U/μL, Sample 2: 0.3 U/μL, Sample 3: 0.03 U/μL, Sample 4: 0.003 U/μL, Sample 5: 0.0003 U/μL, Sample 6: 0.00003 U/μL, Sample 7: 0.000003 U/μL. PNK Stock 30 U/μL (Amersham)

b. Sample Preparation:

A stock mixture containing 24 μL CFTR PCR product of Example 2 (~150 ng/μL), 8 μL phosphorylated GE-1 26-mer (of Example 2, 100 ng/μL), 11 μL VL-5'OH 19-mer (100 ng/μL) having the sequence: 5' HO-GTTTTCCTGGATTAT-GCCT (SEQ. ID#3) and 90 μL of deionized water was aliquotted into 16 μL samples 1 through 7, with 17 μL of the stock solution in Sample 8, the negative control for the experiment. The samples were maintained at 94° C. for 5 min, 60° C. for 2 min, and 16° C. for 2 min.

c. Ligation Reaction:

2 µL of T4 DNA ligase buffer was added to each of the samples. 1 µL of PNK dilutions described above were added to Samples 1 through 7, and 1 µL of T4 DNA ligase (Amersham) was added to each sample as a 1:10 dilution in the T4 DNA ligase buffer. The samples were allowed to ligate overnight at 16° C.

d. Southern Blotting:

The method of Example 2 was followed with the following modifications. Two gels were run for each sample, each gel being blotted separately. On blot was probed with anti-biotin-HRP and the other with anti-biotin-AP.

e. Detection:

Blots to which antibody-HRP conjugates were bound were detected with Lumigen PS-3. The smallest detected quantity of ligation product corresponded to $3 \times 10^{-5}$ U (2.3 amol) of PNK activity on 5 min exposure of X-ray film. Blots to which antibody-AP conjugates were bound were detected with Lumi-Phos Plus. The smallest detected quantity of ligation product corresponded to $3 \times 10^{-5}$ U (2.3 amol) of PNK activity.

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A method for detecting an analyte comprising:
a) performing a specific binding pair reaction for detecting the analyte wherein polynucleotide kinase is present as a label on a specific binding pair member wherein the specific binding pair reaction comprises binding polynucleotide kinase labeled specific binding partner with its cognate specific binding partner for purposes of detecting the analyte, wherein the labeled specific binding partner is the analyte, an analog of the analyte, or a substance having a specific binding affinity for the analyte;
b) reacting polynucleotide kinase, a nucleotide triphosphate and an oligonucleotide having a 5'-OH group and comprising a sequence S2 to phosphorylate oligonucleotide S2 at the 5'-OH group;
c) providing a reaction mixture comprising
  i) oligonucleotide S2,
  ii) a single stranded nucleic acid template comprising contiguous sequence regions C1 and C2,
  iii) a first oligonucleotide having a sequence S1 which is hybridized to region C1 of the template, and
  v) a ligase and a cofactor for the ligase;
d) ligating with the ligase oligonucleotide S1 and oligonucleotide 5'-phosphate S2 to form a ligation product, wherein the ligation only occurs if oligonucleotide S2 is phosphorylated by polynucleotide kinase;

---

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: VC-3 oligomer

<400> SEQUENCE: 1
gggagaaagg cggacaggta        20

<210> SEQ ID NO 2
<211> LENGTH: 26
<212> TYPE: DNA
<213> ORGANISM: Artificial Sequence
<220> FEATURE:
<223> OTHER INFORMATION: GE-1 oligomer

<400> SEQUENCE: 2
agtggaagaa tttcattctg ttctca        26

<210> SEQ ID NO 3
<211> LENGTH: 19
<212> TYPE: DNA
<213> ORGANISM: Artificial Sequence
<220> FEATURE:
<223> OTHER INFORMATION: VL-5' OH oligomer

<400> SEQUENCE: 3
gttttcctgg attatgcct        19 e) detecting the ligated oligonucleotide product of step d as indicating the presence or activity of the polynucleotide kinase; and f) relating the activity of the polynucleotide kinase to the amount of the analyte.

2. The method of claim 1 wherein step c) further comprises adding at least one additional oligonucleotide 5'-phosphate having a sequence complementary to a region of the template, wherein the additional oligonucleotide 5'-phosphates are selected to complementary to contiguous regions of the template C3–Cn, and wherein at least one of the additional oligonucleotide 5'-phosphates is ligated.

3. The method of claim 1 wherein step c) further comprises adding a plurality of oligonucleotide 5' phosphates having sequences S3–Sn, wherein each oligonucleotide 5'-phosphate is complementary to one region of the template C3–Cn, and wherein all oligonucleotide 5' phosphates are ligated.

4. The method of claim 1 wherein each of the oligonucleotide 5'-phosphates consists of the same number of bases and the number of bases is from 2 to 20.

5. The method of claim 4 wherein each of the oligonucleotide 5'-phosphates consists of the same number of bases and the number of bases is from 4 to 12.

6. The method of claim 1 wherein the nucleotide triphosphate used is $\gamma^{32}$P-ATP.

7. The method of claim 1 wherein at least some of the oligonucleotide 5'-phosphates comprise a detectable label.

8. The method of claim 7 wherein the detectable label is selected from radioisotopes, chemiluminescent labels, fluorescent labels, colorimetric labels, enzymes, binding proteins, antigens, antibodies and haptens.

9. The method of claim 1 wherein the ligated product is unlabeled and is detected by a technique which determines its length or number of bases.

10. The method of claim 8 wherein the label is an enzyme and comprising the further steps of reacting the enzyme label present in the ligated product with a substrate for the enzyme and detecting the product of the reaction between the enzyme and the substrate.

11. The method of claim 10 wherein the label enzyme is selected from alkaline phosphatase, β galactosidase, β-glucuronidase, glucose oxidase and horseradish peroxidase.

12. The method of claim 10 wherein the substrate is selected from substrates which produce a colored product, a fluorescent product, chemiluminescence or bioluminescence.

13. The method of claim 1 wherein one of the oligonucleotides selected from S4–Sn is a nonextendable oligonucleotide having a 3'-terminus which can not take part in a ligation reaction.

14. The method of claim 13 wherein the nonextendable oligomer is selected from oligomers which have a dideoxy base at the 3'-end and oligomers which have a blocked 3'-OH group at the 3'-end.

15. The method of claim 1 wherein oligonucleotide S1 contains at least about five bases more than each of oligonucleotides S2–Sn.

16. The method of claim 1 wherein the template is immobilized onto a solid support.

17. The method of claim 16 wherein the solid support comprises magnetic particles.

18. The method of claim 16 wherein the solid support containing the template and hybridized ligated oligonucleotide product is separated from any unhybridized oligonucleotides.

19. The method of claim 1 wherein the polynucleotide kinase is T4 polynucleotide kinase.

20. The method of claim 1 wherein the ligase enzyme is selected from T4 ligase, T7 ligase, Tth ligase, Taq ligase and *E. coli* DNA ligase.

21. The method of claim 20 wherein the ligase enzyme is T4 DNA ligase.

22. The method of claim 1 used for detecting or measuring the activity of polynucleotide kinase.

23. The method of claim 1 wherein the single stranded nucleic acid template is produced by separating a double stranded nucleic acid.

24. The method of claim 1 wherein the ligation proceeds from the 3' end of oligonucleotide S1.

25. The method of claim 1 wherein oligonucleotide S1 contains a 5' phosphate group and the ligation proceeds from the 5' end of oligonucleotide S1.

* * * * *